United States Patent
Schlosberg et al.

[11] Patent Number: 5,997,760
[45] Date of Patent: Dec. 7, 1999

[54] CARBOXYLIC ACID ESTERS AND COMPOSITION COMPRISING THEM

[75] Inventors: Richard Henry Schlosberg, Bridgewater, N.J.; Kirk Christian Nadler, Plaquemine, La.

[73] Assignee: Exxon Chemical Patents Inc., Houston, Tex.

[21] Appl. No.: 08/896,145

[22] Filed: Jul. 17, 1997

[30] Foreign Application Priority Data

Jul. 18, 1996 [GB] United Kingdom ............... 9615086.7

[51] Int. Cl.$^6$ .................... C09K 5/00; C10M 105/38
[52] U.S. Cl. ................... 252/68; 508/485; 560/129
[58] Field of Search ............... 508/485; 252/68; 560/129

[56] References Cited

U.S. PATENT DOCUMENTS

| | | | |
|---|---|---|---|
| 4,032,304 | 6/1977 | Dorer, Jr. et al. | 44/398 |
| 4,175,045 | 11/1979 | Timony | 208/485 |
| 4,248,726 | 2/1981 | Uchinuma et al. | 252/68 |
| 4,826,633 | 5/1989 | Carr et al. | 508/485 |
| 5,185,092 | 2/1993 | Fukuda et al. | 508/485 |
| 5,262,076 | 11/1993 | Ishida et al. | 252/68 |
| 5,391,311 | 2/1995 | Ishida et al. | 252/68 |
| 5,458,794 | 10/1995 | Bardasz et al. | 508/485 |
| 5,733,853 | 3/1998 | Bardasz et al. | 508/485 |

FOREIGN PATENT DOCUMENTS

| | | |
|---|---|---|
| 480479B1 | 3/1997 | European Pat. Off. |
| 22268 | 7/1996 | WIPO |
| WO 96/22268 | 7/1996 | WIPO |

OTHER PUBLICATIONS

Yasamasa Kuwahara et al., 1,3,5,7–Tetramethyldecyl Formate, Larodolure: Aggregation Pheromone of the Acarid Mite, '*Lardoglyphus konoi*', Agricultural and Biological Chemistry, vol. 46, No. 9, pp. 2283–2291, 1982.

Goran Odham, "Synthesis of methyl 2D, 4D, 6D–, 2D,4L, 6D–, 2L,4D, 6D–and 2L, 4L, 6D–trimethylnonanoate", Chemical Abstracts, vol. 68, No. 5, Abstract No. 21482c,: p. 2049, Jan. 29, 1968.

Bertelsen Ola et al., "Chemical composition of the free–flowing secretion of the preen gland of the dipper", Chemical Abstracts, vol. 83, No. 15, Abstract No. 128970x, pp. 289–290, Oct. 13, 1975,.

*Primary Examiner*—Margaret Medley
*Attorney, Agent, or Firm*—Douglass J. Collins

[57] ABSTRACT

Esters of 2,4-dimethylheptanoic and 2,4,6-trimethylnonanoic acids, and their use as lubricants and refrigerant oils.

15 Claims, No Drawings

CARBOXYLIC ACID ESTERS AND COMPOSITION COMPRISING THEM

This invention relates to esters of carboxylic acids and mono- and poly-hydroxy compounds (the latter hereinafter referred to for brevity as polyols), to their use as lubricants, and to compositions containing them.

There has been generally used as a refrigerant fluid in refrigerators, freezers, air-conditioning units, and similar appliances, often referred to generally as refrigerators, a composition comprising one or more chlorofluorocarbons. After the discovery that such molecules contributed to the depletion of the atmospheric ozone layer, they have largely been replaced by chlorine-free fluorocarbons, for example, difluoromethane (HFC32) and 1,1,1,2-tetrafluoroethane (HFC134a).

The introduction of fluorocarbon refrigerants has necessitated other changes in refrigerant compositions, since the lubricating or base oils used with chlorofluorocarbons are not sufficiently compatible with fluorocarbon refrigerants, causing phase separation at some temperatures, usually the lower temperature, in the operating range. As a result, various other lubricants, including mineral oils, polyglycols, alkylbenzenes and, more especially, esters have been proposed as lubricants for refrigerant fluid compositions.

There remains a need, however, for a lubricant having a suitable viscosity for refrigerant fluid applications, which is miscible with the intended refrigerant in the operating temperature range in the proportions used in refrigerant fluid compositions, and which does not suffer from the disadvantages associated with a number of presently available materials. There also remains a need for an improved synthetic lubricant for other end uses, including engine oils, e.g., petrol- and diesel-powered automobile and heavy duty oils, two-stroke oils, and industrial oils, e.g., hydraulic fluids, greases, and power train fluids.

The present invention provides an ester of a polyol and at least one acid selected from the group consisting of 2,4-dimethylheptanoic acid and 2,4,6-trimethylnonanoic acid. These acids will occasionally herein be referred to for brevity as a specified acid. The invention also provides an ester of the specified $C_{12}$ acid with a monohydric alcohol.

Esters of $C_9$ and $C_{12}$ acids in general are less water-sensitive than esters of lower carbon number acids, and accordingly less corrosive toward metal and less aggressive toward seals. Esters of the specified $C_9$ acid are generally less viscous than those of 3,5,5 trimethylhexanoic, and more viscous than those of nonanoic, acid, offering a useful intermediate group of properties between these two commercially available groups of materials.

Referring more especially to the polyol, the hydroxyl groups are in certain embodiments advantageously esterified to an extent giving a final hydroxyl number (mg KOH/g) of at most 10, and preferably at most 5, and preferably each converted hydroxyl group is esterified by 2,4-dimethylheptanoic acid or 2,4,6-trimethylnonanoic acid. Advantageously all the hydroxyl groups of the polyol are esterified by the same specified acid.

In further embodiments, however, the present invention provides an ester in which a proportion of hydroxyl groups is left free to yield a material with a hydroxyl number within the range of from 10 to 180, advantageously from 10 to 100. It has been found that such an ester has improved surface activity when used as an engine lubricant additive, providing improved fuel economy and reduced wear, and adds oxidation stability to the lubricant formulation.

With one exception, however, esters in which some only of the hydroxyl groups are esterified by a specified acid are within the scope of the invention. In U.S. Pat. No. 5,262,076, Ishida et al., assigned to Nippon Oil Co. Ltd., there is disclosed as a comparative example a tetraester of pentaerythritol, 2-methylhexanoic acid and 2,4-dimethylheptanoic acid.

As preferred examples of polyol, there may be mentioned those having up to 6 hydroxyl groups, since above this number the viscosity of the resulting esters tends to be higher than the optimum. The polyol advantageously has a carbon number within the range of from 2 to 12, more especially 2 to 8. Aliphatic, especially saturated aliphatic, alcohols are preferred. Polyols having some degree of steric hindrance are preferred, examples of these being neopentyl glycol, pentaerytiritol, dipentaerythritol, tripentaerythritol, trimethylol-ethane, -propane, and -butane, and 2-ethyl-2-methyl- and 2,2-diethyl-1,3-propanediol and 2,2,4-trimethylpentane-1,3-diol. Other preferred polyols are 2,2-dimethylol butane, ethylene glycol, propylene glycol, 1,4-butanediol, and polyalkylene glycols (e.g., polyethylene, -propylene or -butylene glycol, blends thereof or copolymerized mixtures of the monomeric compounds). Other, somewhat less preferred, examples are other 2-substituted propanediols, other substituted or unsubstituted butanediols, pentanediols, hexanediols, heptanediols and octanediols and polyoxyalkylene glycols. Mixtures of two or more such polyols may also be used. More complex examples of polyols are oligomers or polymers of a mono- or poly-hydroxy acid optionally with one or more of the polyols mentioned above.

The specified acids, which are known per se (CA Registration Nos. 2624-25-1 for the $C_9$ acid and 3005-07-0 for the $C_{12}$ acid) are advantageously obtained by, for example, multiple aldol condensation of propanal, selective hydrogenation of ethylenic unsaturation of the resultant trimeric or tetrameric unsaturated aldehyde to yield a saturated aldehyde, and oxidation of the aldehyde to the desired acid, as described in WO 96/22268, the entire disclosure of which is incorporated herein by reference and to which the reader is referred for a more detailed description of the procedure. The procedure enables the production of the specified acids either separately or in admixture with each other, and also, if desired, in admixture with 2-methylpentanoic acid, which if present provides, when esterified, valuable properties to compositions comprising the esters according to the invention.

The molecular weight of the ester is desirably in the range of from 300 to 3000, advantageously 300 to 2000.

The esters may be produced by methods known per se or described in the literature from the alcohol and the relevant acid or acid chloride, anhydride, or other derivative, optionally in the presence of a solvent. Elevated temperatures and reduced pressures may be employed to drive the reaction toward completion by removal of the water produced. Catalysts may be employed. Suitable catalysts include, for example, a titanium catalyst, e.g., a tetraalkyl titanate, especially tetra-iso-propyl or tetraoctyl ortho titanate, or a sulphonic acid, e.g., p-toluene sulphonic acid or methylsulphonic acid. Any catalyst present in the reaction product may be removed by aqueous alkali treatment. Conversion is advantageously such that the final hydroxyl number is below 10, and preferably below 5.

Advantageously, in order to minimize corrosion, stability, and haze problems in use, the residual acid number is reduced to below 3 (mg KOH/g), most preferably below 0.05, and the metal content advantageously to below 25 ppm, preferably to below 5 ppm. Advantageously, the resistivity of the product is at least $10^{12}$, and preferably at least $10^{13}$, ohm.cm.

These acid and metal values may be achieved by purification by contacting the ester with, for example, silica gel, activated carbon, a zeolite, a clay or activated alumina.

As indicated above, although the hydroxyl groups of the polyols are advantageously all esterified by a specified acid, one or more may be esterified by another acid or other acids. As examples of such other acids, there may be mentioned, more especially, straight or branched chain aliphatic mono or polycarboxylic acids, although the molar proportion of the latter, based on the total of the esterifying acids, should be limited to at most 25%, preferably at most 20%, to avoid gelation of the ester. The other acids advantageously contain from 4 to 14 carbon atoms, including carboxylic carbon atoms. As examples, there may be mentioned the straight chain alkanoic acids having from 4 to 14 carbon atoms, their corresponding iso acids, 2-ethyl- and 2-methyl-hexanoic, 5-ethylhexanoic, 3,5,5-trimethylhexanoic, 2-ethylpentanoic, trimethylacetic, 2-, 3- and 4-methyl pentanoic, 2-ethyl-, 2,2-dimethyl-, and 3,3-dimethylbutanoic and 2,2-dimethylactanoic acids, and oxo octanoic acid. Typical polycarboxylic acids include adipic, azelaic, sebacic, 1,1,2-dodecanedioic, phthalic and trimellitic acids. Mixtures of polyols may also be employed with mixtures of acids.

As indicated above, it is within the scope of the invention to provide mixed esters in which at least one hydroxyl group of the polyol is esterified by a specified acid and another or the other is esterified by another acid, for example, one listed above; the invention also provides mixtures of two or more esters according to the invention and mixtures of one or more esters according to the invention and one or more esters not according to the invention, the latter being, for example, an ester of a polyol and an acid or acids other than either of the specified acids. All such mixtures are useful as synthetic lubricants.

Advantageously, the viscosity of the composition at 100° C. is within the range of from 1 to 30 cSt (mm2/s).

As indicated above, there is also provided an ester of 2,4,6-trimethylnonanoic acid and a monohydric alcohol, especially an alkanol, especially an alcohol having at least 3 carbon atoms, especially from 4 to 20, more especially from 4 to 10, carbon atoms. These esters have utility as lubricants and lubricant components in the same manner as do the esters of polyhydric alcohols, Advantageously, they have acid and hydroxyl numbers and metal contents as expressed above as advantageous or preferable for the polyhydric alcohol esters.

The invention also provides a composition comprising an ester according to the invention and a fluorocarbon refrigerant. As examples of refrigerant there may be mentioned HFC 134a, HFC 32, HFC 134 (1,1,2,2-tetrafluroethane), HFC 143 (1,1,2-trifluoroethane), HFC 143a (1,1,1-trifluoroethane), HFC 152 (1,2-difluoroethane) and HFC 152a (1,1-difluoroethane).

Advantageously the ester and the fluorocarbon are present in proportions of from 1:99 to 30:70, preferably from 1:99 to 25:75, by weight.

The refrigerant composition, and a composition comprising an ester of the invention, or an ester containing mixture described above may also contain other components, e.g., anti-wear agents (e.g. substituted phosphoro-thionates, sulphides, ZDDP's), extreme pressure agents, (e.g., phosphate esters) antioxidants (e.g., amines, phosphates) corrosion inhibitors (e.g., stearates, succinic acid derivatives), metal deactivators (e.g., benzotriazoles), rust preventives (e.g., sulphonates), detergents (sulphonates, salicylates, phenates), dispersants, VI improvers, pour point depressants and antifoams (e.g., silicones).

The invention further provides the use of an ester of a polyol and a specified acid as a lubricant or as a component of a refrigerant composition.

We claim:

1. A polyol ester, each hydroxyl group of the polyol being esterified by an acid selected from 2,4-dimethylheptanoic acid and 2,4,6-trimethylnonanoic acid.

2. An ester as claimed in claim 1, wherein the polyol has up to 6 hydroxyl groups.

3. An ester as claimed in claim 1, wherein the polyol has from 2 to 12 carbon atoms.

4. An ester as claimed in claim 1, wherein the polyol is neopentyl glycol, pentaerythritol, dipentaerythritol, tripentaerythritol, trimethylol propane or trimethylolethane.

5. An ester as claimed in claim 1, which has an acid number below 3 mg KOH/g, a hydroxyl number below 10 mg KOH/g and a metals content below 25 ppm.

6. A polyol ester, at least one hydroxyl group of the polyol being esterified by an acid selected from 2,4-dimethylheptanoic acid and 2,4,6-trimethylnonanoic acid, other than a tetraester of pentaerythritol, 2,4-dimethylheptanoic acid, and 2-methylhexanoic acid.

7. An ester as claimed in claim 6, wherein the polyol has up to 6 hydroxyl groups.

8. An ester as claimed in claim 6, wherein the polyol has from 2 to 12 carbon atoms.

9. An ester as claimed in claim 6, wherein the polyol is neopentyl glycol, pentaerythritol, dipentaerythritol, tripentaerythritol, trimethylol propane or trimethylolethane.

10. An ester as claimed in claim 6, which has a hydroxyl number of from 10 to 180 KOH/g.

11. An ester as claimed in claim 1, which has a viscosity at 100° C. within the range of 1 to 30 mm2/s.

12. A refrigerate oil lubricating composition comprising an ester as defined in claim 1, and a fluorocarbon refrigerant.

13. A refrigerate oil lubricating composition as claimed in claim 12, wherein the refrigerant is HFC 134a.

14. A lubricating composition as claimed in claim 12, wherein the ester:refrigerant weight ratio is within the range of from 1:99 to 30:70.

15. A lubricating composition comprising an ester as defined in claim 1, and at least one member selected from the group consisting of anti-wear agents, antioxidants, corrosion inhibitors, metal deactivators, rust preventers, detergents, dispersants, VI improvers, pour point depressants, and antifoams.

* * * * *

UNITED STATES PATENT AND TRADEMARK OFFICE
CERTIFICATE OF CORRECTION

PATENT NO. : 5,997,760
DATED : December 7, 1999
INVENTOR(S) : Schlosberg et al

It is certified that error appears in the above-identified patent and that said Letters Patent is hereby corrected as shown below:

title, line 2, -- COMPOSITION -- should read "COMPOSITIONS"

col. 4, line 43, claim 12, -- refrigerate -- should read "refrigerant"

col. 4, line 45, claim 13, -- refrigerate -- should read "refrigerant"

Signed and Sealed this

Twenty-fifth Day of July, 2000

Attest:

Q. TODD DICKINSON

Attesting Officer

Director of Patents and Trademarks